United States Patent [19]

Cope et al.

[11] Patent Number: 5,064,428
[45] Date of Patent: Nov. 12, 1991

[54] MEDICAL RETRIEVAL BASKET

[75] Inventors: Constantin Cope, Elkins Park, Pa.; Scott E. Boatman; Joseph W. Roberts, both of Bloomington, Ind.

[73] Assignee: Cook Incorporated, Bloomington, Ind.

[*] Notice: The portion of the term of this patent subsequent to Oct. 15, 2008 has been disclaimed.

[21] Appl. No.: 584,474

[22] Filed: Sep. 18, 1990

[51] Int. Cl.$^5$ .............................................. A61B 17/22
[52] U.S. Cl. ................................................ 606/127
[58] Field of Search ................ 606/127; 128/772, 657; 604/282, 164

[56] References Cited

U.S. PATENT DOCUMENTS

| 4,425,908 | 1/1984 | Simon | 128/1 R |
|---|---|---|---|
| 4,601,705 | 7/1986 | McCoy | 604/94 |
| 4,619,246 | 10/1986 | Molgaard-Nielsen et al. | 128/1 R |
| 4,741,335 | 5/1988 | Okada | 606/127 |

OTHER PUBLICATIONS

Hodgson, DE, *Using Shape Memory Alloys*, Shape Memory Applications, Inc., Cupertino, CA, 1988, pp. 18-19.
"Stone Removal," *COOK Diagnostic and Interventional Products for Radiology, Cardiology, and Surgery*, Cook Incorporated, Bloomington, Ind., 1986, p. 3.

Cope, C. "Novel Nitinol Basket Instrument for Percutaneous Cholecystolithotomy," *American Journal of Roentgenology*, 155:515-516, Sep., 1990.

*Primary Examiner*—William E. Kamm
*Assistant Examiner*—Scott R. Akers
*Attorney, Agent, or Firm*—Richard J. Godlewski

[57] ABSTRACT

A stone retrieval basket having superelastic metallic alloy wires attached to the distal end of an inner elongaged member tube for retrieving calculi and crushing them against an outer introducer tube percutaneously inserted into a patient. The basket comprises kink-resistant superelastic metallic alloy wires such as nitinol forming a bulbous shape for capturing calculi therein. The ends of the superelastic wires of the basket are attached to the distal end of a inner elongated member tube with the aid of sleeves crimped thereon, which are soldered or spot welded in recesses about the distal end of the inner tube. The outer tube is percutaneously inserted into the biliary or urinary system in which the basket is then inserted to capture large-sized stones. A peel-away sheath is also included to introduce the basket and inner elongatged member tube into the outer introducer tube. A dilator member, which is extendable through the passageway of the inner tube, removes any residual debris from the tube that may be left during the stone removal procedure.

21 Claims, 2 Drawing Sheets

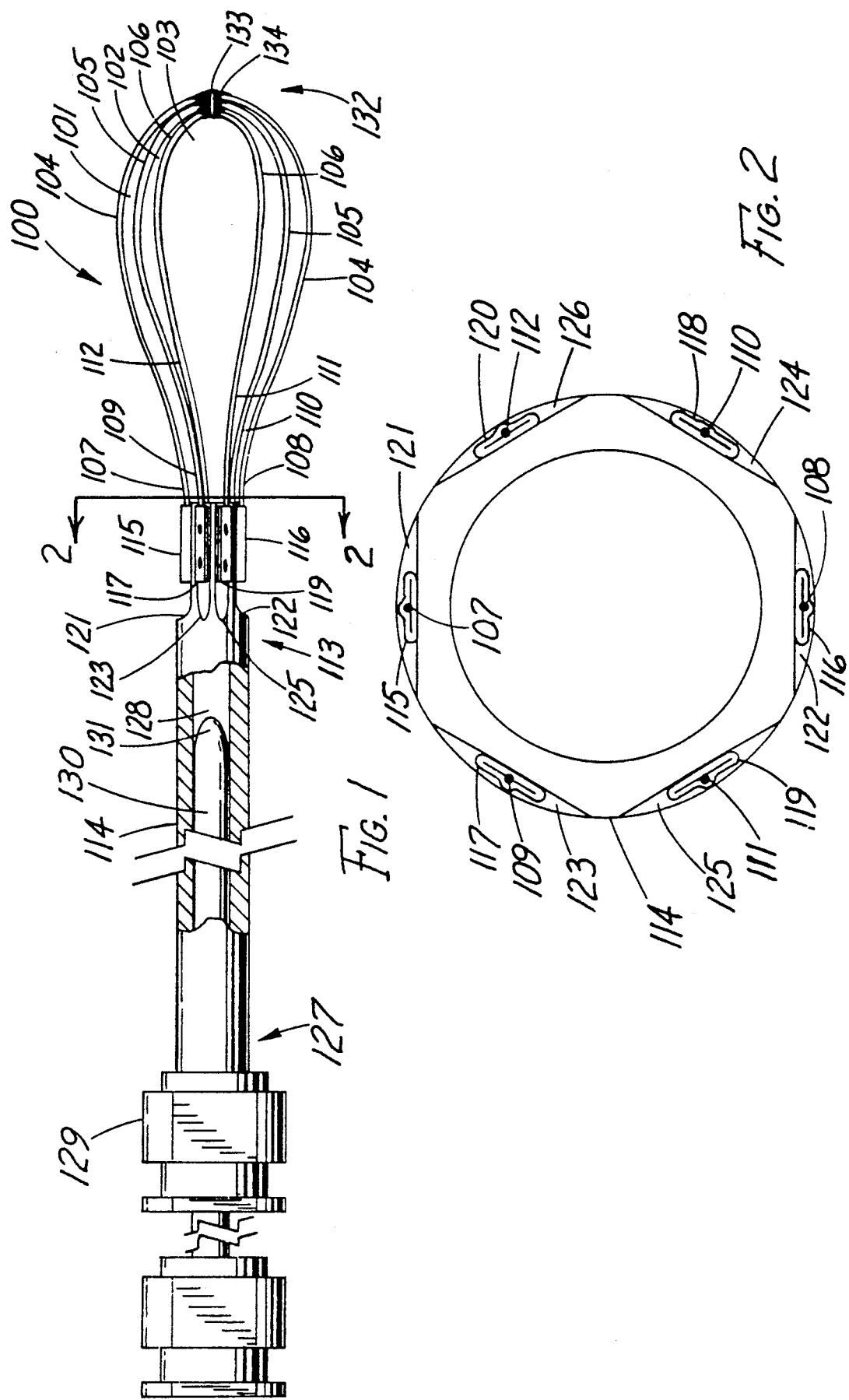

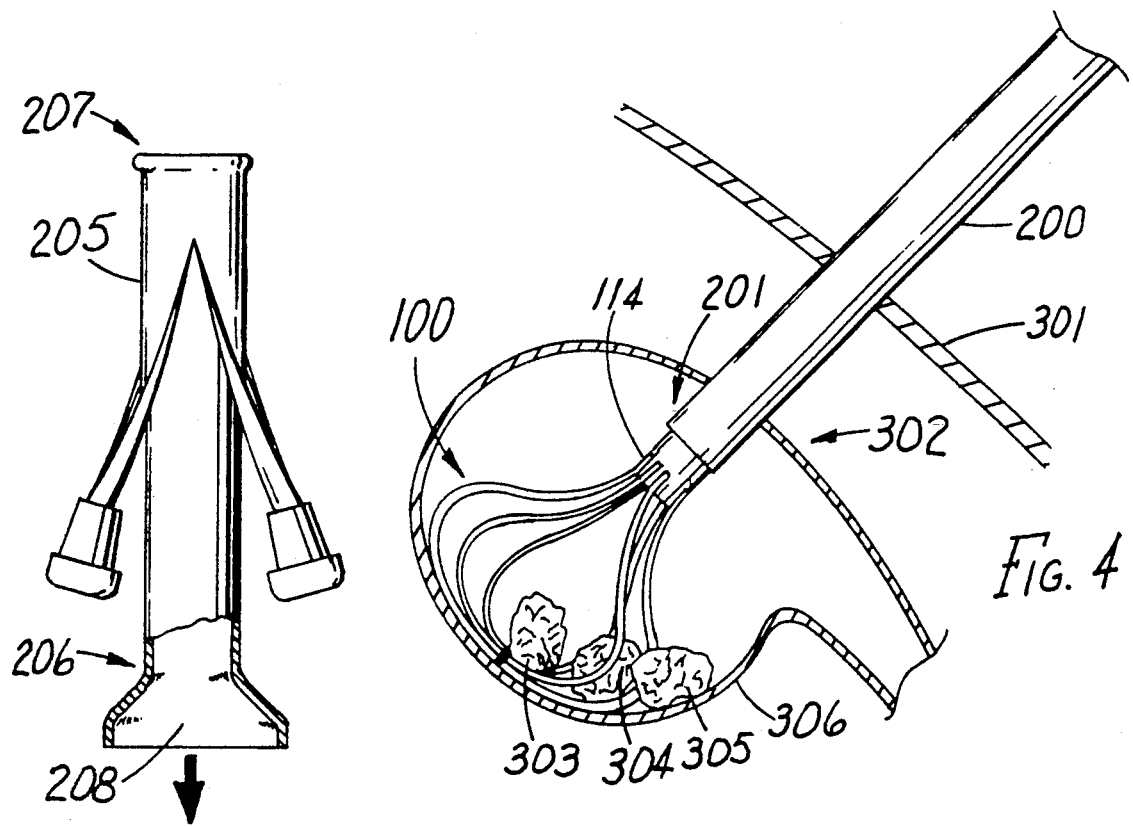
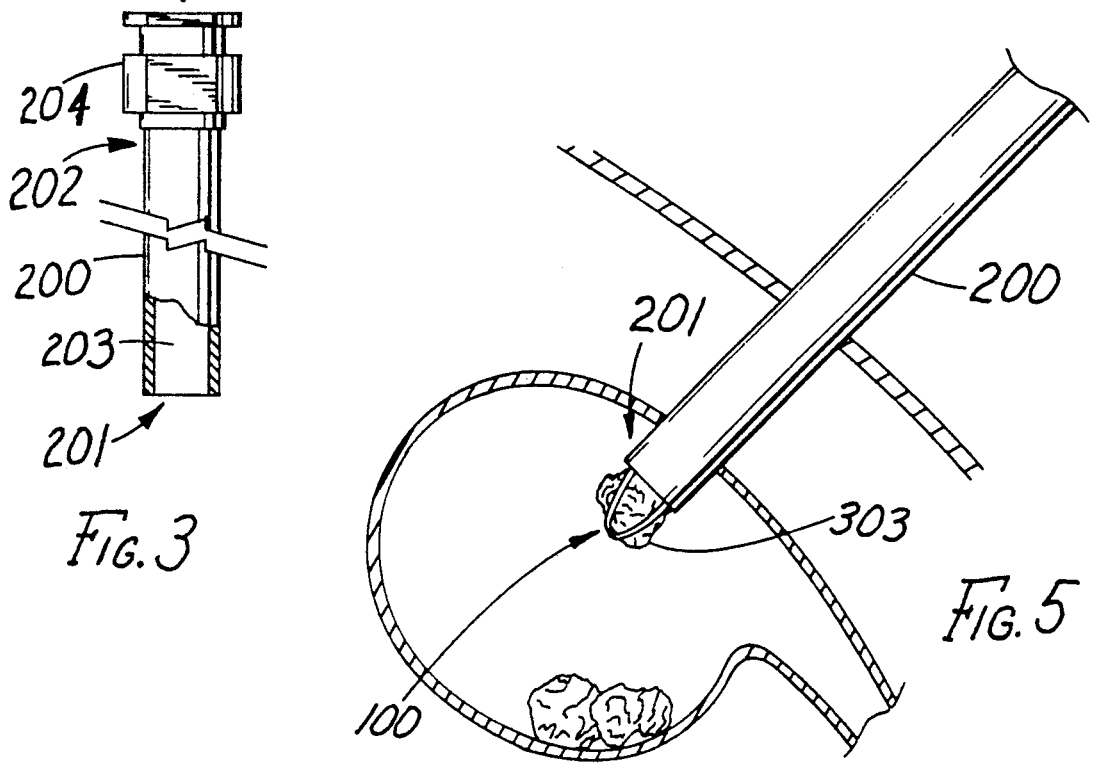

MEDICAL RETRIEVAL BASKET

TECHNICAL FIELD

This invention relates to catheters and, in particular, a stone basket attached to the distal end of a catheter for retrieving calculi and the like from organs, cavities, and ducts of the body.

BACKGROUND OF THE INVENTION

Gallstones are a common problem in the United States and the most frequent cause of gallbladder inflammation. Calculi in other parts of the biliary system are also common place as are calculi in the urinary system. Several percutaneous and open surgical procedures are available for removing calculi from the biliary or the urinary system. With respect to the biliary system, one invasive, open surgical procedure is known as cholecystectomy or choledocholithotomy in which the gallbladder is removed along with any stones from the common duct. A T tube is commonly inserted in the duct for removal of residual calculi. However, this procedure is, as are other open surgical procedures, subject to an extensive recovery period lasting anywhere from two to six weeks.

Minimally invasive surgical procedures that utilize percutaneous access include, for example, a percutaneous cholecystolithotomy in which calculi are removed from the gallbladder through a percutaneously inserted access sheath. Several postoperative access routes such as transcholedochal, transcystic, and transcholecystic are employed for removing biliary stones from the gallbladder, cystic duct, or common duct. In such cases, the extractions are carried out through the fistula tract left by a T tube. The percutaneous extraction is based on the use of forceps or basket-tipped catheters. Forceps enable a quick extraction of stones within reach. Furthermore, forceps facilitate crushing large-sized stones and extracting compacted stones. One problem with forceps is that they cannot negotiate double or triple curves or the exaggerated tortuosities of fistula tracks. This problem is partially overcome with the basket-tipped catheter to overcome such winding courses, but it is frequently not possible to seize the large-sized or impacted stones.

A problem with most basket-tipped catheters or stone retrieval baskets arises in the case of very small or flat stones or when the stones lie in large cavities where they have ample room for displacement. Most stone extraction baskets are of the helically shaped variety for permitting entry of the stone only from the side of the basket. This is because the tip of the basket, which usually contains a small length of cannula or a fastener for holding the ends of the wire basket together, is too sharp and inefficient for a head-on or an open-ended approach.

With presently available open-ended baskets in which the wires of the basket form an open loop to provide a head-on retrieval, the basket wire is comprised of stainless steel, which is subject to kinking and does not have the desired resiliency for more than one stone capture.

With respect to large-sized stones, the overall size of the basket is also limited due to the tendency of the stainless steel wire to kink.

SUMMARY OF THE INVENTION

The foregoing and other problems are solved and a technical advance is achieved by an illustrative stone retrieval basket having a plurality of superelastic alloy wires attached to the distal end of an elongated member tube, each wire forming a loop extending longitudinally and distally from the tube for advantageously providing an open leading end capture of calculi in body cavities, organs, and ducts. The superelastic basket wire is extremely kink-resistant and permits repeated capture of calculi without kinking. The kink-resistant wire also affords much larger sized baskets than presently available stainless steel wire baskets.

The retrieval basket comprises inner and outer elongated member tubes each having a hollow passageway therein for capturing and breaking up large calculi contained within the superelastic alloy wire basket. The basket comprises at least two superelastic alloy wires each having their ends attached to the distal end of the inner member tube and forming a loop extending longitudinally and distally from the inner member tube. The superelastic metallic alloy wire loops are interconnected distally to form the basket.

The hollow passageway of the outer elongated member tube is sized for positioning the interconnected wire loops as well as the inner elongated member tube therein for capturing large calculi within the wire loop basket.

The basket further comprises a third superelastic metallic alloy wire having its ends attached to the distal end of the inner member tube for forming a third loop extending longitudinally and distally from the inner member tube. The third loop being interconnected distally to the first and second loops. A fastener such as suture thread interconnects the superelastic wire loops distally while advantageously providing flexibility for the basket loops to capture calculi with a head-on or open-ended approach. The fastener further includes a urethane material for coating the suture material and wires to fixedly position the loops with respect to each other and to advantageously maintain the flexible distal end of the basket for capturing calculi.

The superelastic metallic alloy wire of the basket is formed in a shape approximating that of a light bulb or pear in which the basket has a longitudinal length approximately twice as long as its lateral width for advantageously capturing calculi particularly in large or flat bottom cavities.

The basket wires illustratively comprise a nickel-titanium alloy such as nitinol, which exhibits a superelastic property when maintained at a temperature above its transformation temperature. The transformation temperature of the superelastic basket wire is selected to be below the normal operating temperature of the basket to maintain the basket wire in a superelastic state. In such state, the superelastic basket wires advantageously return to their original shape when a deformation stress is removed from the wire. The superelastic alloy wire also increasingly resists deformation as the stress load is increased. When nitinol wire is operated below its transformation temperature, heat must be applied to return the alloy wire to its original shape. Advantageously, the operating temperature of the superelastic alloy wire of the present basket is above its transformation temperature to resist kinking and to return to its original shape without the application of any heat thereto.

The inner and outer elongated member tubes of the basket are comprised of a metal such as stainless steel to permit the crushing or breaking up of large calculi. The attachment of the superelastic nickel-titanium alloy wire by soldering or welding is extremely difficult. Advantageously, a metallic sleeve or small section of cannula is crimped about each end of each basket wire and attached to the distal end of the inner member tube in recesses formed thereabout by spot welding or soldering. The attachment of each end of the superelastic wire to a recess permits the wire basket and inner member tube to be easily inserted into the passageway of the outer elongated member tube.

The basket also further includes a TEFLON peel-away introducer sheath for percutaneously inserting the wire basket into the outer elongated member tube.

When inserted into the fundus of the gallbladder or a bile duct, the basket is extended beyond the distal end of the outer member tube to capture a stone. The basket with a contained stone is drawn into the passageway of the outer member tube to lodge the stone between the distal end of the outer tube and the basket wires. The lodged stone is then crushed or decomposed through the inner member tube passageway. Instruments are inserted through the inner member passageway to remove the stone fragments.

The basket further includes a metallic dilator rod having a bullet-shaped distal end for cleaning debris and the like from the passageway of the inner member tube.

BRIEF DESCRIPTION OF THE DRAWING

FIG. 1 depicts a medical retrieval basket of the present invention for capturing large-sized calculi;

FIG. 2 depicts a front view of the distal end of the basket of FIG. 1 along the line 2—2;

FIG. 3 depicts an outer elongated member tube for use with the basket of FIG. 1 and an introducer sheath for inserting the basket therein;

FIG. 4 depicts the retrieval basket of the present invention inserted into the fundus of a patient's gallbladder for capturing gall stones therein; and FIG. 5 depicts the medical retrieval basket of the present invention with a captured stone therein lodged at the distal end of the outer member tube for crushing and subsequent removal.

DETAILED DESCRIPTION

Depicted in FIG. 1 is a medical stone retrieval basket 100 comprising three loops 101-103 of respective superelastic metallic alloy wires 104-106 attached to distal end 113 of inner elongated member tube 114 for capturing and crushing relatively large-sized calculi found typically in the biliary and urinary systems. The stone basket is also suitable for use in other cavities, ducts, passages and organs of the human body. Each of the superelastic metallic alloy wires 104-106 comprises a nickel-titanium alloy having a transformation temperature below that of the normal operating environment. In particular, each of superelastic metallic alloy wires 104-106 is comprised of nitinol wire available from Shape Memory Applications, Inc., Sunnyvale, Calif. The transformation temperature of this particular wire is 8° C., which is well below the body temperature of patients in which the wire is inserted into for capturing and crushing calculi.

Depicted in FIG. 2 is a front view of distal end 113 of inner elongated member tube 114 along the line 2—2. As depicted in FIGS. 1 and 2, the two ends 107, 108; 109, 110; and 111, 112 of respective wires 104-106 are attached to the distal end 113 of inner elongated member tube 114 using respective sleeves 115,116; 117,118; and 119, 120 of stainless steel tube crimped thereon. Distal end 113 of inner elongated member tube 114 includes flat recesses 121-126 formed therein for attaching crimped sleeves 115-120, respectively. The crimped sleeves are attached to the tube in these recesses by spot welds or solder. The outer surface of the distal end may also be circumferentially reduced to accept the crimped sleeves.

By way of example, each of nitinol wires 104-106 comprises a 17 cm length of wire having a 0.010" diameter with a 5 mm length of 24 gauge regular wall stainless steel tube crimped on each end thereof. The attached wires form light bulb or pear-shaped loops 101-103. The longitudinal length of each loop is approximately 5 cm and extends distally from distal end 113 of the inner elongated member tube 114. The lateral width of each loop is approximately 2.5 cm.

Inner elongated member tube 114 comprises a 22 cm length of 8 gauge regular wall stainless steel tube having distal end 113, proximal end 127, and hollow passageway 128 extending longitudinally therebetween. A well-known female Luer lock connector 129 is fixedly attached to proximal end 127 of the inner elongated member tube in a well-known manner.

Also depicted in FIGS. 1 and 2 in hollow passageway 128 of the inner elongated member tube is dilator member 130 having a bullet-shaped distal end 131 which when fully inserted, extends 1-2 cm beyond the distal end of the inner elongated member tube for cleaning calculi and debris from hollow passageway 128.

At the distal end 132 of basket 100, suture material 133 joins loops 101-103 together to form the basket. A urethane material 134 coats the suture material and the wires of the basket to fixedly position the wires relative to each other.

Depicted in FIG. 3 is outer elongated member tube 200 of a 20 cm length of 5 gauge regular wall stainless steel tube having a distal end 201, proximal end 202, and hollow passageway 203 extending longitudinally therebetween. A female Luer lock connector 204 is fixedly attached in a well-known manner to the proximal end of the tube. In a minimally invasive surgical procedure, outer elongated member tube 200 is inserted percutaneously into the fundus of the gallbladder. Basket 100 and the distal end of inner elongated member tube 114 are inserted into outer tube passageway 203 with the aid of peel-away sheath 205. When a stone is captured in basket 100, the captured stone and basket are lodged against the distal end 201 of the outer elongated member tube. Other well-known surgical instruments are then inserted through inner member tube passageway 128 to crush or break up the lodged stone.

Also depicted in FIG. 3 is a peel-away sheath 205 for inserting the retrieval basket and inner elongated member tube into passageway 203 of the outer elongated member tube. The peel-away sheath has a flared distal end 206, which abuts next to the proximal end of female Luer lock connector 204. The flare assists in aligning the longitudinal axes of peel-away sheath 205 and inner elongated member tube 114. The peel-away sheath also has a proximal end 207 for receiving and compressing basket 100 into hollow passageway 208 which extends longitudinally through the peel-away sheath. This peel-away sheath is commercially available from Cook Incorporated, Bloomington, Ind.

Depicted in FIG. 4 is outer elongated member tube 200 percutaneously inserted through outer tissue layers 301 and fundus 302 of a gallbladder. The percutaneous insertion of the outer elongated member tube into the fundus of the gallbladder is performed with a well-known surgical procedure. A number of large-sized calculi or gallbladder stones 303-305 are also depicted lying in the lower portion of the gallbladder on wall 306. Inner elongated member tube 114 with stone retrieval basket 100 attached thereto extends beyond the distal end 201 of the outer elongated member tube. The basket is pressed against lower fundus wall 306 to enlarge the bulbous shape of the basket and capture large-sized gallbladder stone 303. The superelastic metallic alloy wire of the basket permits enlargement of the bulbous shape to permit head-on or side access of calculi into the basket. Furthermore, the bulbous shape, such as that of a light bulb or pear, permits the basket to be placed directly against the wall of an organ and capture stones positioned thereagainst. The superelastic wires of the basket prevent its collapse when it is deformed during the exploratory maneuvers needed for retrieving stones in different parts of the gallbladder. The physician rotates and manipulates the basket to capture the stone in the basket and draws the captured stone against the distal end of the outer elongated member tube.

Depicted in FIG. 5 is outer elongated member tube 200 with calculi 303 captured in basket 100 and lodged against the distal end 201 of the outer tube. The physician will insert a chemical or other well-known surgical means to dissolve, break up or crush the stone and remove the stone fragments through the hollow passageway of the inner member tube. The superelastic metallic alloy wire of the basket does not kink as with stainless steel wire baskets. This superelastic property of the wire permits the repeated capture and pick up of all the stones and stone fragments within the organ cavity. As previously described, dilator member 130 is inserted through passageway 128 into the inner member tube to clear any debris or stone fragments from the passageway. The inner member tube may also be removed from the outer member 200 to provide the use of forceps or other mechanical retrieval means for retrieving broken up stone fragments or smaller stones within the organ cavity.

It is to be understood that the above-described retrieval basket is merely an illustrative embodiment of the principles of this invention and that other catheters and retrieval baskets attached thereto may be devised by those skilled in the art without departing from the spirit and scope of this invention. In particular, the basket can be preformed into any desired shape or size for capturing and removing calculi from the biliary or urinary system. In addition, other rigid materials may be utilized for the inner and outer elongated member tubes to facilitate breakage or crushing of large-sized stones. It is also contemplated that any number of basket wires may be utilized and attached to flexible or rigid material catheters.

What is claimed is:

1. A medical retrieval basket comprising:
  a first elongated member having a proximal end, a distal end, and a hollow passageway longitudinally positioned therebetween;
  a first superelastic metallic alloy wire having first and second ends attached to said distal end of said first elongated member and forming a first loop extending longitudinally and distally from said distal end of said member; and
  a second superelastic metallic alloy wire having first and second ends attached to said distal end of said member, forming a second loop extending longitudinally and distally from said distal end of said member, and interconnected distally to said first loop.

2. The basket of claim 1 further comprising a second elongated member having a hollow passageway longitudinally positioned therein, in which the first elongated member and said wires are removably inserted.

3. The basket of claim 1 further comprising a third superelastic metallic alloy wire having first and second ends attached to said distal end of said first elongated member, forming a distal end of said member, and being interconnected distally to said first and second loops.

4. The basket of claim 3 further comprising a fastener interconnecting distally said first, second, and third loops.

5. The basket of claim 4 wherein said fastener includes suture material interconnecting said first, second, and third loops.

6. The basket of claim 5 wherein said fastener further includes a urethane coating material about said suture material and said wires.

7. The basket of claim 1 wherein said distal end of said first elongated member has a plurality of recesses in an outer surface thereof, each recess having an individual one of said ends of said first and second wires attached therein.

8. The basket of claim 7 wherein each of said superelastic wire ends includes a metallic sleeve crimped thereon, each of said sleeves being attached to said distal end in an individual one of said plurality of recesses.

9. The basket of claim 1 further -comprising a peel-away sheath having a hollow passageway with said first and second loops positioned therein in a collapsed state.

10. The basket of claim 1 wherein each of said first and second wires comprises a nickel-titanium alloy.

11. The basket of claim 1 further comprising a second elongated member having a bullet shaped distal end and removably inserted in said passageway.

12. The basket of claim 1 wherein said first elongated member comprises a stainless steel tube.

13. The basket of claim 1 wherein each of said first and second loops has a length and a width, said length being approximately twice as long as said width.

14. A medical retrieval basket comprising:
  a first tube having a first proximal end, a first distal end, and a first passageway longitudinally positioned therebetween;
  a second tube having a second proximal end, a second distal end, and a second passageway longitudinally positioned therebetween and removably inserted in said first passageway;
  a first superelastic metallic alloy wire having first and second ends attached to said second distal tube end and forming a first loop extending longitudinally and distally from said second distal tube end;
  a second superelastic metallic alloy wire having first and second ends attached to said second distal tube end and forming a second loop extending longitudinally and distally from said second distal tube end;
  a third superelastic metallic alloy wire having first and second ends attached to said second distal tube end and forming a third loop extending longitudinally and distally from said second distal tube end; and a fastener interconnecting distally said first, second, and third loops.

15. The basket of claim 14 wherein said first tube passageway is sized for retracting said first, second, and third loops therein.

16. The basket of claim 14 wherein each of said first, second, and third wires comprises a nickel-titanium alloy.

17. The basket of claim 14 further comprising a peel-away sheath having a hollow passageway with said first, second, and third loops positioned therein in a collapsed state.

18. The basket of claim 14 wherein said second distal tube end has a plurality of recesses equally spaced from one another in an outer surface thereof.

19. The basket of claim 18 wherein each of said wire ends includes a sleeve crimped thereon, each of said sleeves being attached to said second distal tube end in an individual one of said recesses.

20. The basket of claim 14 further comprising an elongated member having a bullet-shaped distal end and removably inserted in said second tube passageway.

21. A medical retrieval basket comprising:
a first metal tube having a first proximal end, a first distal end, and a first hollow passageway longitudinally positioned therebetween;
a second metal tube having a second proximal end, a second distal end, and a second hollow passageway longitudinally positioned therebetween and removably inserted in said first tube passageway, said second distal tube end having first, second, and third pairs of oppositely facing recesses formed in an outer surface thereof and equally spaced from one another;
first, second, and third nitinol wires each having a superelastic state and a pair of ends attached to one of said pairs of oppositely facing recesses, each of said ends having a metal sleeve crimped thereto, each of said sleeves being attached to said second distal tube end in an individual one of said recesses, said first, second, and third wires forming respective first, second, and third loops extending longitudinally and distally from said second distal tube end and having a width and a length approximately twice as along as said width;
suture and a urethane coating fixedly interconnecting said first, second and third loops at a farmost distal position thereof, said first tube passageway being sized for retracting said wires therethrough;
a peel-away sheath having a hollow passageway with said first, second, and third loops positioning therein in a collapsed state; and
an elongated member having an elliptically shaped distal end and removably inserted in said second tube passageway.

* * * * *